US010624763B2

(12) United States Patent
Conley

(10) Patent No.: US 10,624,763 B2
(45) Date of Patent: Apr. 21, 2020

(54) ORTHOPAEDIC IMPACTOR WITH RADIALLY EXPANDING THREADING

(71) Applicant: Symmetry Medical Manufacturing, Inc., Warsaw, IN (US)

(72) Inventor: Jonathon G. Conley, Silver Lake, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 540 days.

(21) Appl. No.: 14/511,735

(22) Filed: Oct. 10, 2014

(65) Prior Publication Data

US 2016/0100956 A1   Apr. 14, 2016

(51) Int. Cl.
*A61F 2/46* (2006.01)
*A61F 2/30* (2006.01)

(52) U.S. Cl.
CPC .. *A61F 2/4609* (2013.01); *A61F 2002/30484* (2013.01); *A61F 2002/4629* (2013.01); *A61F 2002/4681* (2013.01)

(58) Field of Classification Search
CPC ........ A61F 2/32; A61F 2/4609; A61F 2/4637; A61F 2002/4619; A61F 2002/4624; A61F 2002/4628; A61F 2002/4629; A61F 2002/4638; A61B 17/1666; A61B 17/1746; A61B 17/92; A61B 2017/922; A61B 2017/924
See application file for complete search history.

(56) References Cited

U.S. PATENT DOCUMENTS

| | | | |
|---|---|---|---|
| 5,683,399 A | 11/1997 | Jones | |
| 5,954,727 A * | 9/1999 | Collazo | A61F 2/4609 606/91 |
| 7,043,808 B2 | 5/2006 | Patton | |
| 7,621,921 B2 * | 11/2009 | Parker | A61F 2/34 606/91 |
| 7,934,415 B2 | 5/2011 | Smida et al. | |
| 8,142,439 B2 | 3/2012 | Parker | |
| 8,277,457 B1 | 10/2012 | Burgi et al. | |
| 8,464,574 B2 * | 6/2013 | Smida | G01M 13/005 73/37 |
| 2005/0038443 A1 | 2/2005 | Hedley et al. | |
| 2009/0192515 A1 * | 7/2009 | Lechot | A61F 2/4609 606/91 |

FOREIGN PATENT DOCUMENTS

EP      1 000 595 A1    5/2000

* cited by examiner

*Primary Examiner* — Kevin T Truong
*Assistant Examiner* — Tracy L Kamikawa
(74) *Attorney, Agent, or Firm* — Taylor IP, P.C.

(57) ABSTRACT

An orthopaedic impactor includes an elongate member having a first end and a second end; a striking surface connected to the first end; an actuator held by the elongate member; and an impaction assembly held by the elongate member at the second end. The impaction assembly includes a collar that has an opening formed through; an interfacing member that has a threaded end and is split into at least four sections held partially within the opening, the interfacing member having an expansion opening formed to the threaded end that defines a center; and a separator held in alignment with the expansion opening and connected to the actuator. The separator is configured to radially expand the at least four sections away from the center when advanced through the expansion opening by the actuator.

14 Claims, 5 Drawing Sheets

ORTHOPAEDIC IMPACTOR WITH RADIALLY EXPANDING THREADING

BACKGROUND OF THE INVENTION

1. Field of the Invention

The present invention relates to surgical devices, and, more particularly, to orthopaedic impactors.

2. Description of the Related Art

The hip joint is configured as a ball and socket arrangement which includes the femoral head joined to the natural socket or acetabulum located in the pelvis. Deterioration of the acetabulum and/or femoral head can be brought about by injury or progressive diseases such as osteoarthritis. When injury or disease occurs, the damaged component(s) can be replaced or rebuilt using appropriate orthopaedic implants. In the technique known as a "total hip replacement," one method involves cementing or press-fitting an acetabular cup prosthesis into the acetabulum after the acetabulum has been sufficiently reamed to accept the cup. Additionally, fixation fasteners can be used to hold the cup in the acetabulum, and the cup can include a porous coating on the convex side to promote bone ingrowth. The femoral head can also typically be replaced.

In order to properly seat an acetabular cup into the acetabulum an impaction tool, or impactor, is used by the surgeon to firmly seat the cup. The impactor needs to securely hold the cup while the cup is being located in the acetabulum, and the impactor also needs to securely hold the cup while the cup is being impacted into the acetabulum. The acetabular cup impactor can include a surgical implement coupler which can be secured to the acetabular cup. An elongated shaft is joined to the surgical implement coupler at one end, and includes a striker cap at the opposite end of the shaft. The cup is seated in the prepared acetabulum by positioning the cup in the prepared depression, and imparting a series of blows from a mallet against the striker cap. The force of the blows is transmitted through the shaft of the impactor, to seat the cup in the prepared opening in the acetabulum. After the cup is properly seated, the surgical implement coupler of the impactor is detached from the cup.

Particularly in a minimally invasive procedure, where a small incision is made to reduce the trauma to surrounding tissue, at least two problems occur in seating an acetabular cup. It is difficult to properly align the impactor because of anatomical features that are in the way, and disconnecting the head from the cup is more difficult with limited access to the end of the tool. Cleaning and sterilization of the impactor after surgery can also be difficult.

U.S. Pat. No. 7,621,921 to Parker describes a split thread orthopaedic implant impactor. The impactor includes a shaft having a proximal end and a distal end with a trigger that is pivotably connected to the distal end. The trigger has a cam end which connects to a push rod within the shaft. The trigger actuates the push rod to engage and release an implant, such as an acetabular cup, by pushing a wedge between a threaded pair to increase the radius of the threaded pair and removing the wedge from between the threaded pair of decrease the radius of the threaded pair. The impactor described by Parker is effective to quickly release an attached implant, but the use of a wedge to spread the threaded pair apart requires sections of the threaded pair to be unthreaded which does not provide as much threading engagement between the male thread of the threaded pair and the female thread of the implant and can cause the strength of the connection to be reduced.

What is needed in the art is an orthopaedic impactor that can releasably connect to an implant and has increased connection strength with the connected implant.

SUMMARY OF THE INVENTION

The present invention provides an impactor with an interfacing member that has a threaded end and is split into at least four sections.

The invention in one form is directed to an orthopaedic impactor including an elongate member having a first end and a second end; a striking surface connected to the first end; an actuator held by the elongate member; and an impaction assembly held by the elongate member at the second end. The impaction assembly includes a collar that has an opening formed through; an interfacing member that has a threaded end and is split into at least four sections held partially within the opening, the interfacing member having an expansion opening formed to the threaded end that defines a center; and a separator held in alignment with the expansion opening and connected to the actuator. The separator is configured to radially expand the at least four sections away from the center when advanced through the expansion opening by the actuator.

The invention in another form is directed to an impaction assembly for seating an orthopaedic implant that includes a collar having an opening formed through and a connector configured to connect to an orthopaedic impactor; an interfacing member having a threaded end and being split into at least four sections held partially within the opening, said interfacing member having an expansion opening formed to the threaded end that defines a center; and a separator held in alignment with the expansion opening and having an actuating end, the separator being configured to radially expand the at least four sections away from the center when advanced through the expansion opening by a force applied to the actuating end.

An advantage of the present invention is that an attached implant can be quickly and easily detached from the orthopaedic impactor.

Another advantage is that splitting the interfacing member into at least four sections allows for a more complete threading to be formed on the surface of the interfacing member, which increases the connection strength between the interfacing member and a connected implant.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 1:
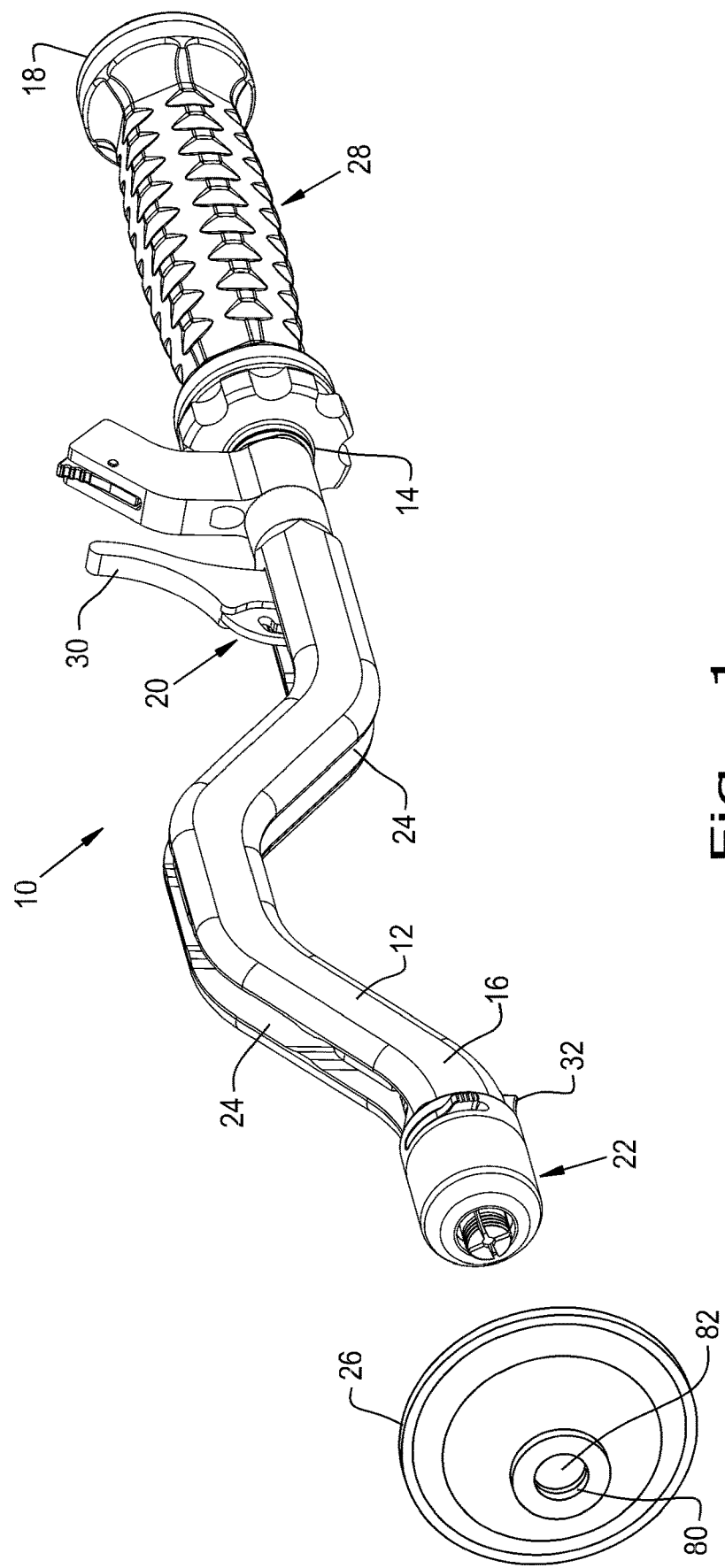
FIG. 1 is a perspective view of an embodiment of an orthopaedic impactor according to the present invention.

Referring now to the drawings, and more particularly to FIG. 1, there is shown an orthopaedic impactor 10 which generally includes an elongate member 12 with a first end 14 and a second end 16, a striking surface 18 connected to the first end 14, an actuator 20 held by the elongate member 12, and an impaction assembly 22 held at the second end 16. The elongate member 12, shown here as a shaft, can include offsets 24 to allow for easier navigation of an implant 26, shown here as an acetabular cup, to the desired implantation location within a patient. The acetabular cup 26 is shown as not being connected to the orthopaedic impactor 10 for ease of illustration, but during implantation would be temporarily connected to the orthopaedic impactor 10 so that the acetabular cup 26 can be press fit into a prepared anatomical site using the orthopaedic impactor 10. The striking surface 18 provides a surface for a user to strike with a tool, such as a mallet, to provide impaction force that is transmitted to a connected acetabular cup through the orthopaedic impactor 10. The striking surface 18 can be included on a handle 28 connected to the elongate member 12 or could be an integral part of the elongate member 12. As the orthopaedic impactor 10 will be used in surgical applications where bodily fluids will be present, it is useful if all of the components of the orthopaedic impactor 10 are formed from materials that are sufficiently strong to impact the acetabular cup 26, or other implant, into a desired anatomical location and are also biocompatible. Such materials are known for surgical applications and can include stainless steel, cobalt chromium, titanium, ultra-high molecular weight polyethylene, and polyether ether ketone. The components of the orthopaedic impactor 10 can be fabricated utilizing any method that allows for the proper shapes and sterilization of the components to be achieved, and can include machining, molding, punching, etc.

The orthopaedic impactor 10 includes an actuator 20 held by the elongate member 12. As shown, the actuator 20 can include a trigger 30 that is linked to an actuating portion 32 held at the second end 16 of the elongate member 10 adjacent to the impaction assembly 22. The actuator 20, as shown, is configured so that the trigger 30 can rotate toward and away from the elongate member 10, with rotation toward the elongate member 10 causing the actuating portion 32 to be linearly displaced in a direction toward the first end 14 and rotation away from the elongate member 10 causing the actuating portion 32 to be linearly displaced in a direction away from the first end 14. Such an actuator 20 is shown and described in more detail in U.S. Pat. No. 7,621,921, which is owned by the Applicant and incorporated herein by reference. It should be appreciated that the actuator 20 shown and described is exemplary only and could be replaced by a differently configured actuator that is capable of connecting to the impaction assembly 22 in order to effectuate connection and disconnection of the acetabular cup 26 to the impaction assembly 22, which will be described below.

Figure 2:
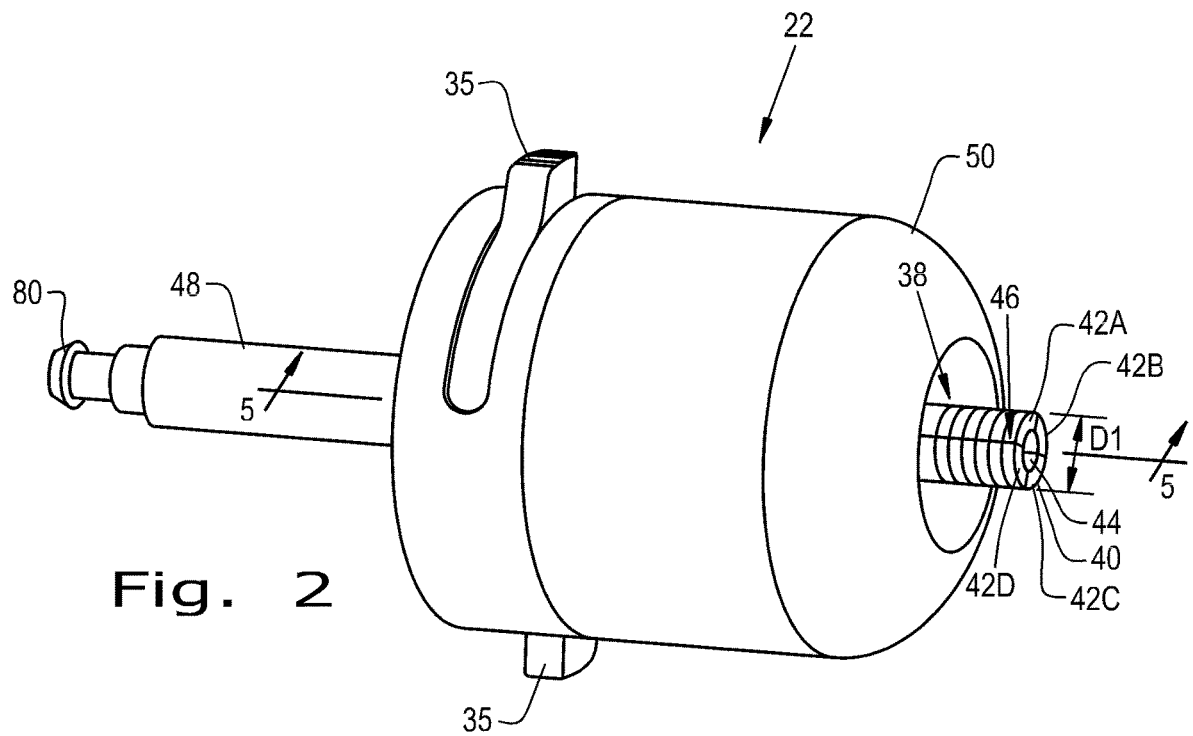
FIG. 2 is a perspective view of an embodiment of an impaction subassembly according to the present invention with a minimized threading radius.
Figure 3:
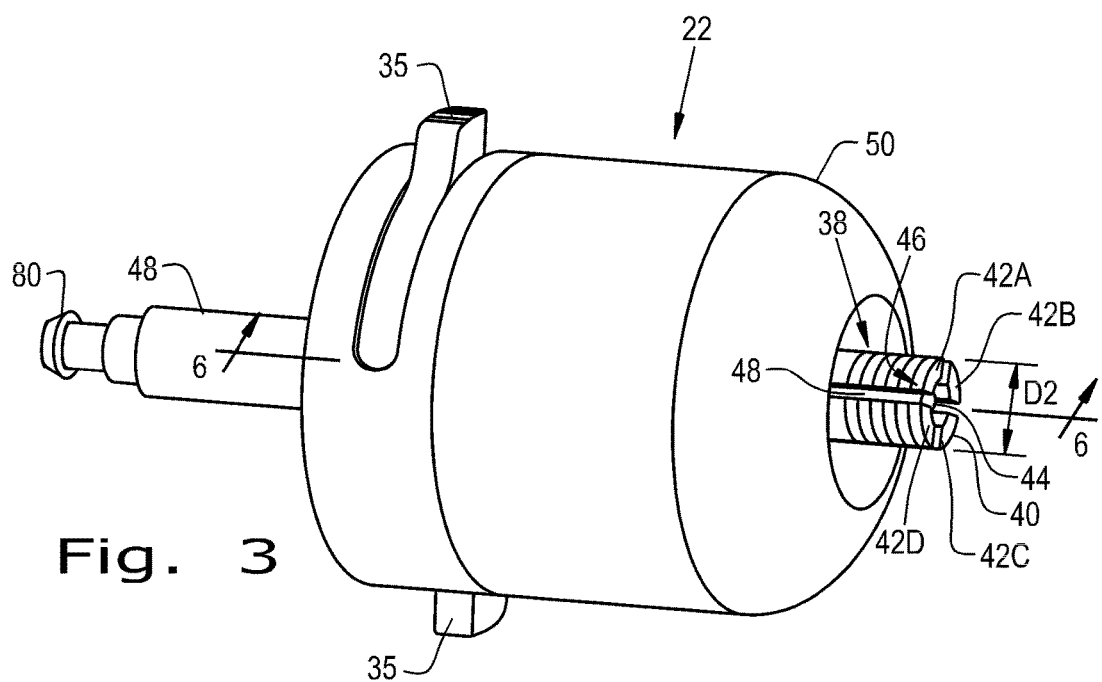
FIG. 3 is a perspective view of the impaction subassembly shown in FIG. 2 with a maximized threading radius.

Referring now to FIGS. 2-6, the impaction assembly 22 is shown in greater detail. As can be seen, the impaction assembly 22 includes a collar 34 that has an opening 36 formed through. The collar 34 includes connectors 35, shown as connecting tabs, that allow for the impaction assembly 22 to be held by the elongate member 12. If desired, the connecting tabs 35 could also be formed as an integral piece of the collar 34. The connecting tabs 35 shown are exemplary only and any other type of connector(s) could be included on the collar 34 to securely connect the impaction assembly 22 to the elongate member 12. An interfacing member 38 is partially held within the opening 36. The interfacing member 38 has a threaded end 40 that extends out of the opening 36 and is split into four sections 42A, 42B, 42C and 42D. While the interfacing member 38 is shown as being split into four sections 42A, 42B, 42C and 42D, the interfacing member 38 could be split into more than four sections, if desired, which will be described below. The interfacing member 38 is split such that the sections 42A, 42B, 42C and 42D congregate together around an expansion opening 44 which defines a center of the interfacing member 38. As can be seen, the interfacing member 38 is configured as having a cylindrical shape defined about the expansion opening 44, which extends longitudinally through the interfacing member 38. While the interfacing member 38 is shown as having a cylindrical shape, other shapes could be utilized without straying from the scope of the present invention. The described and shown sections 42A, 42B, 42C and 42D are shaped as approximately identical wedges that each form an approximately 90 degree arc relative to the expansion opening 44, which defines the center of the interfacing member 38. It should be appreciated that if the interfacing member 38 is split into more than four sections, each section will not form an approximately 90 degree arc relative to the expansion opening 44. Alternatively, the four or more sections of the interfacing member 38 could be non-identical so that one or more of the sections forms an arc relative to the expansion opening 44 that is different than the arc(s) formed by the other sections. As shown in FIGS. 2 and 3, the sections 42A, 42B, 42C and 42D together form a threading 46 of the threaded end 40 with a variable threading diameter. As shown in FIG. 2, the sections 42A, 42B, 42C and 42D are all in contact with each other and have a minimum threading diameter D1. As shown in FIG. 3, the sections 42A, 42B, 42C and 42D have been spaced apart from each other by a separator 48 of the impaction assembly 22, which increases the threading diameter to an expanded threading diameter D2.

Figure 4:
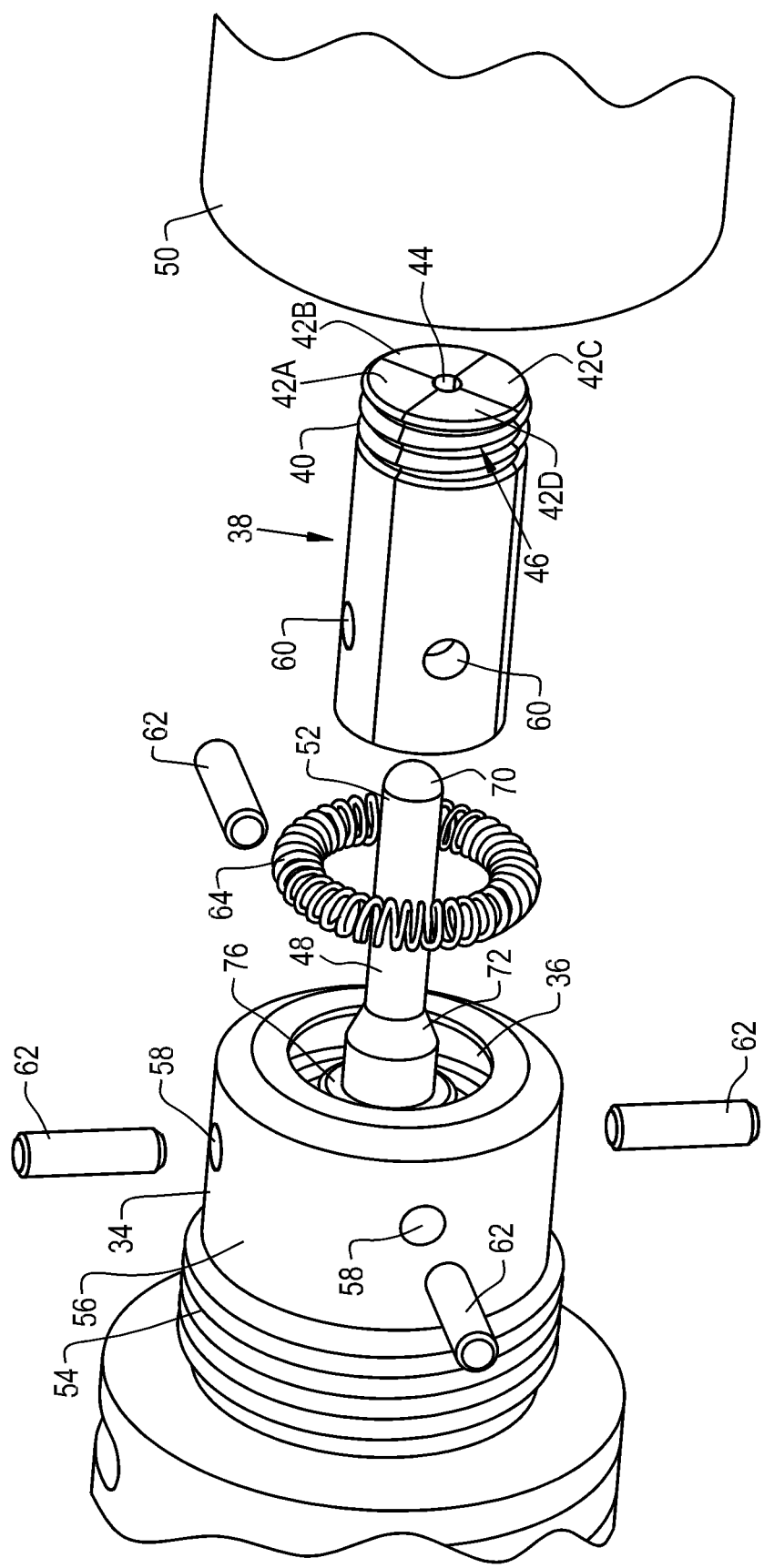
FIG. 4 is a partially exploded perspective view of the impaction subassembly shown in FIGS. 2 and 3.
Figure 5:
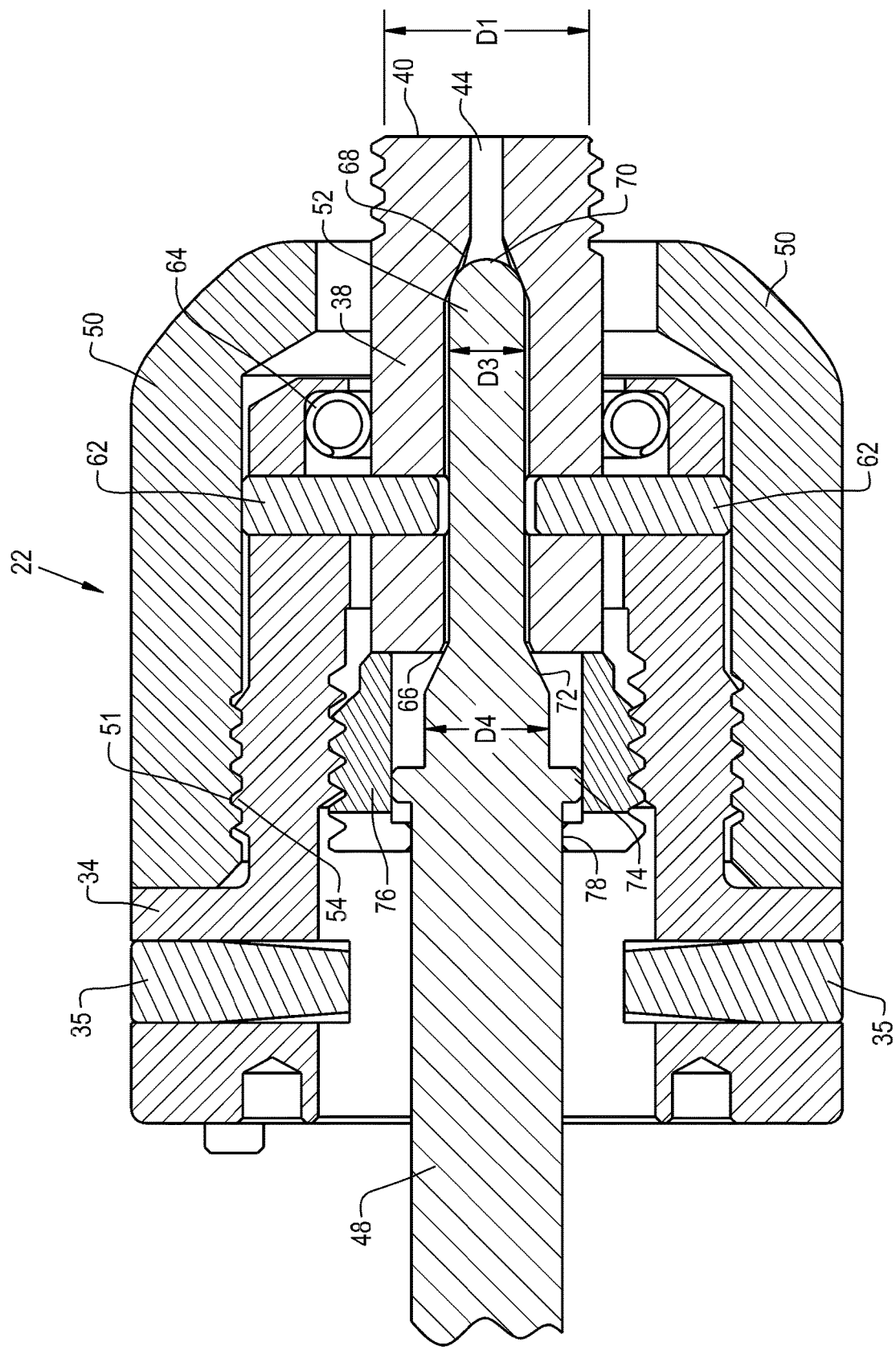
FIG. 5 is a cross-sectional view of the impaction subassembly shown in FIG. 2 taken along line 5-5.
Figure 6:
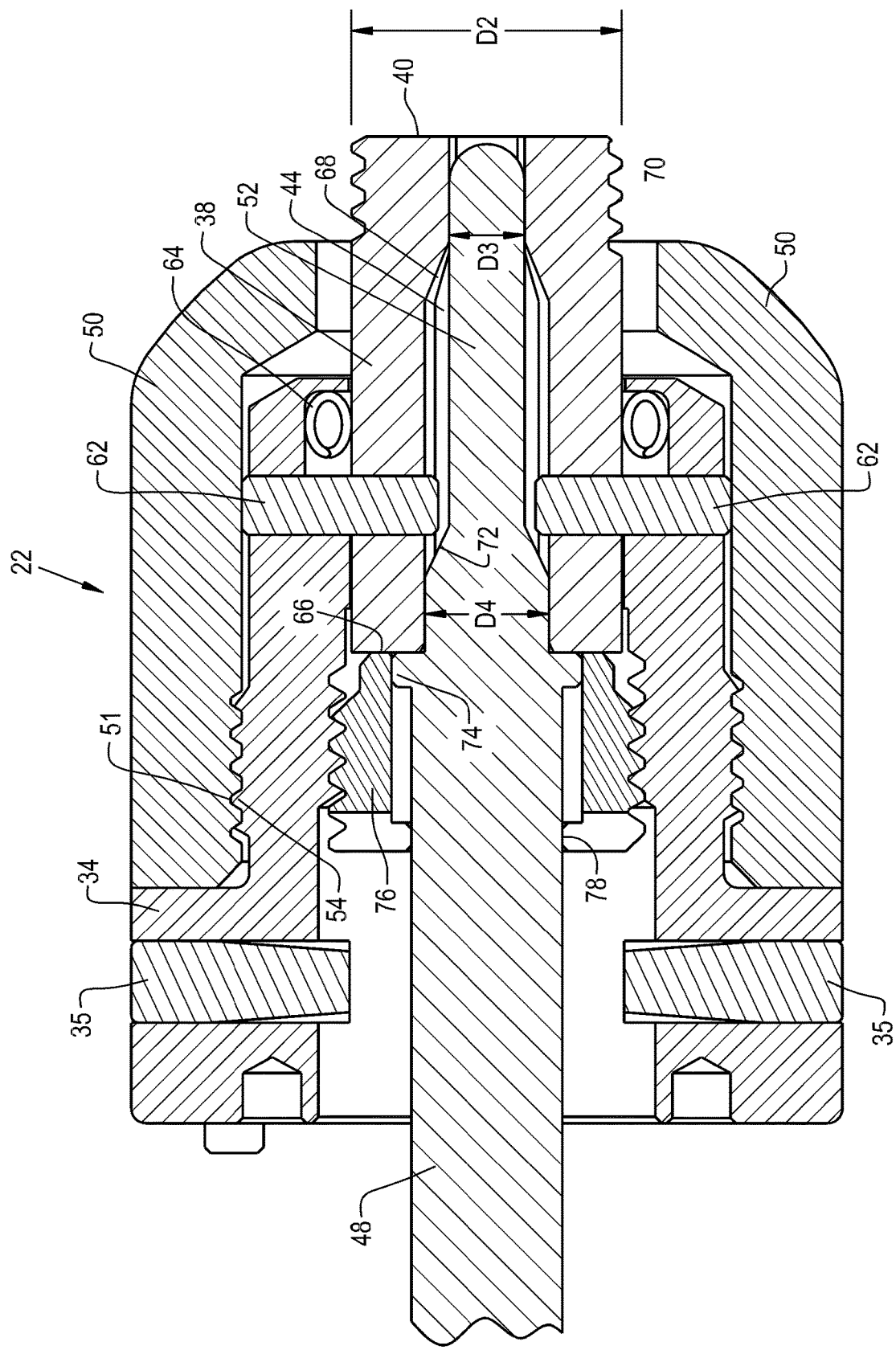
FIG. 6 is a cross-sectional view of the impaction subassembly shown in FIG. 3 taken along line 6-6.

The collar 34 is connected to a shell 50 in FIGS. 2 and 3 that obscures a complete view of the impaction assembly 22, so further reference is made to FIGS. 4-6. The shell 50 is useful to include since it provides a larger surface area that can be utilized to transfer impaction force from the orthopaedic impactor 10 to an attached implant, but is not necessary to seat the implant within the desired anatomical location. As can be seen in an exploded view of a portion of the impaction assembly 22 in FIG. 4, the separator 48, which is shown as a push rod, is held in alignment with the expansion opening 44 of the interfacing member 38 so that the separator 48 can have an expanding portion 52 advanced through the expansion opening 44. The separator 48 is connected to the actuator 20 so that the actuator 20 can cause linear movement of the separator 48 relative to the collar 34 and through the expansion opening 44. The separator 48 can be connected to the actuator 20 at any location and in any fashion that allows this motion, such as the actuator 20 pushing on a connecting end 80 of the separator 48. The collar 34 can have a collar threading 54 formed on an outer surface 56 that will mate with threading 51 on the shell 50 so that the shell 50 can be connected to the collar 34. Pin openings 58 can be formed through the outer surface 56 to opening 36 and pin openings 60 can be formed through sections 42A, 42B, 42C and 42D of the interfacing member 38 that will align with pin openings 58 when the interfacing member 38 is held within the opening 36. Pins 62 can be placed through pin openings 58 and aligned pin openings 60 to help hold the sections 42A, 42B, 42C and 42D within the opening 36. A biasing member 64, shown as a coiled spring, can be included in the opening 36 and surround one or more of the sections 42A, 42B, 42C and 42D to bias the sections 42A, 42B, 42C and 42D toward the center of the interfacing member 38 and resist uncontrolled expansion of the interfacing member 38. Although shown as a coiled spring, the biasing member 64 could be any sort of element that can push the sections 42A, 42B, 42C and 42D together and be deformed so that the sections 42A, 42B, 42C and 42D can be radially expanded away from the expansion opening 44.

Referring now to FIG. 5, a cross-sectional view of the impaction assembly 22 where the threaded end 40 has a minimized threading diameter D1 is shown. As can be seen, the expansion opening 44 of the interfacing member 38 defines an opening width which can be variable along the length of the interfacing member 38. The opening width of the expansion opening 44 is greatest at an end 66 of the interfacing member 38 opposite the threaded end 40, which allows for the expanding portion 52 of the separator 48 to rest within the expansion opening 44 without radially expanding the sections 42A, 42B, 42C and 42D away from the expansion opening 44. The interfacing member 38 can have a tapering portion 68, where the opening width of the expansion opening 44 decreases to a minimum toward the threaded end 40. After the expanding portion 52 of the separator 48 passes the minimum opening width of the expansion opening 44, the interfacing member 38 has an expanded threading diameter D2, as shown in FIG. 3. The separator 48, which is shown as a push rod, can also have a varying diameter along its length. As can be seen, the expanding portion 52 of the push rod 48 has a rod diameter D3 that extends to a tip 70 of the push rod 48. The push rod 48 can also have a tapered portion 72 where the diameter of the push rod 48 increases to a second push rod diameter D4 that is greater than rod diameter D3 in order to cause further radial expansion of the threaded end 40 of the interfacing member 38. When the push rod 48 includes tapered portion 72 and increases in diameter to second push rod diameter D4, the expanded diameter D2 of the threaded end 40 is at a maximum when the portion of the push rod 48 with second push rod diameter D4 is held within the expansion opening 44, as shown in FIG. 6. In this regard, a push rod 48 with a smaller rod diameter D3 and a larger second push rod diameter D4 can expand the diameter of the threaded end 40 a greater amount than a push rod with a single rod diameter D3 without having to narrow the expansion opening 44. A stop 74 can be formed on the push rod 48 that has a diameter greater than second push rod diameter D4 and will abut against the end 66 of the interfacing member 38 to prevent further advancing of the push rod 48 through the expansion opening 44, as shown in FIG. 6. To prevent the push rod 48 from being pulled out of alignment with the expansion opening 44, a threaded washer 76 with an opening 78 with a diameter that is slightly larger than second push rod diameter D4 can be threaded into the collar 34 so that it surrounds the push rod 48. The stop 74 on the push rod 48 has a greater diameter than the diameter of the opening 78, which prevents the push rod 48 from being advanced out of the opening 78 of the threaded washer 76.

To use the orthopaedic impactor 10 of the present invention, the actuator 20 advances the push rod 48 through the expansion opening 44 of the interfacing member 38 so that the sections 42A, 42B, 42C and 42D are radially forced away from the expansion opening 44 and the threaded end 40 has expanded diameter D2, as shown in FIG. 3. The expansion of the sections 42A, 42B, 42C and 42D is chosen so that the threaded end 40 with expanded diameter D2 can interface with female implant threading 80 formed in an implant opening 82 of the orthopaedic implant 26. The orthopaedic implant 26 is then threaded onto the threaded end 40 so that the orthopaedic implant 26 is securely fastened to the orthopaedic impactor 10. The orthopaedic impactor 10 is then guided to an anatomical structure so that the orthopaedic implant 26 is aligned with a prepared anatomical location for impaction. A user hits the striking surface 18 to force the orthopaedic implant 26 into the prepared anatomical location, until the orthopaedic implant 26 is securely held within the prepared anatomical location. Once the orthopaedic implant 26 is securely held and the user wishes to detach the orthopaedic implant 26 from the orthopaedic impactor 10, the actuator 20 is used to pull the push rod 48 away from the threaded end 40 so that the sections 42A, 42B, 42C and 42D can be advanced back toward the expansion opening 44 and the threaded end 40 has minimized threading diameter D1. Once the threaded end 40 has the minimized threading diameter D1, the threading 46 of the threaded end 40 releases from the female implant threading 80 and the orthopaedic implant 26 is released from the orthopaedic impactor 10. The orthopaedic impactor 10 can then be removed from the patient for cleaning. It should be appreciated that the impaction assembly 22 of the present invention can be configured as a modular component that could be used in many different styles of orthopaedic impactors without straying from the scope of the present invention.

By splitting the interfacing member 38 into four or more sections 42A, 42B, 42C and 42D, the threading 46 of the interfacing member 38 that interfaces with the female implant threading 80 can more entirely cover the threaded end 40 of the interfacing member 38. This increased coverage increases the surface area of the threading 46 of the interfacing member 38 that is interacting with the female implant threading 80, allowing for a more secure connection between the interfacing member 38 and the orthopaedic implant 26. Further, having more identical sections can allow for a smaller separation between adjacent sections when a cylindrical interfacing member 38 is radially expanded, which can allow for greater surface contact between the threading 46 of the interfacing member 38 and the female implant threading 80. This is due to the expansion being radially away from the expansion opening 44, so that the separation each section will experience away from adjacent sections will be equal to the total change in the circumference of the interfacing member 38 divided by the number of sections that the interfacing member 38 is split into. Therefore, having a greater number of sections can allow for less interruption in the threading 46 of the interfacing member 38.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic impactor, comprising:
   an elongate member having a first end with a first axis extending therethrough, a second end, and at least one offset between said first end and said second end wherein the at least one offset defines at least in part first and second sections obliquely angled with respect to the first axis and extending to an interconnecting section at a location offset from said first axis;
   a striking surface connected to said first end;
   an actuator held by said elongate member; and
   an impaction assembly held by said elongate member at said second end, said impaction assembly including:
      a collar having an opening formed through and at least four pin openings formed through an outer surface of the collar to the opening;
      an interfacing member having a threaded end and being split into at least four sections held partially within said opening, said interfacing member having an expansion opening formed to said threaded end that defines a center, each of said at least four sections having a section pin opening that aligns with a respective pin opening of the collar to form a pair of aligned openings;
      at least four pins, each of said at least four pins being placed in a respective pair of aligned openings to hold the sections within the opening of the collar; and
      a separator held in alignment with said expansion opening and connected to said actuator, said separator being configured to radially expand said at least four sections away from said center when advanced through said expansion opening by said actuator, wherein said separator is a push rod including a tapered portion where a diameter of the push rod increases from a first rod diameter to a second rod diameter that is greater than said first rod diameter, said push rod being configured to increase a threading diameter of said threaded end to a maximum when a portion of said push rod with said second rod diameter is held within said expansion opening.

2. The orthopaedic impactor according to claim 1, wherein said threading diameter is minimized when said separator is not advanced through said expansion opening.

3. The orthopaedic impactor according to claim 1, further comprising a biasing member held within said opening and at least partially surrounding said interfacing member, said biasing member being configured to force at least one of said at least four sections toward said center.

4. The orthopaedic impactor according to claim 1, wherein said expansion opening is defined by an opening width.

5. The orthopaedic impactor according to claim 4, wherein said opening width is variable.

6. The orthopaedic impactor according to claim 5, wherein said opening width is smallest adjacent to said threaded end.

7. The orthopaedic impactor according to claim 6, wherein said interfacing member has a maximum expansion when said separator is advanced into said smallest opening width.

8. The orthopaedic impactor according to claim 1, wherein said push rod has a tip.

9. The orthopaedic impactor according to claim 8, wherein said diameter of said push rod is smallest at said tip.

10. The orthopaedic impactor according to claim 9, wherein said push rod has a stop formed thereon that defines a largest diameter of said push rod and is configured to prevent further advancing of said push rod through said expansion opening.

11. The orthopaedic impactor according to claim 1, wherein said interfacing member has a cylindrical shape defined about said center.

12. The orthopaedic impactor according to claim 11, wherein said interfacing member is split into four wedges and each said wedge forms a 90 degree arc relative to said center.

13. The orthopaedic impactor according to claim 11, wherein at least one section of said at least four sections forms an arc that is not equal to 90 degrees relative to said center.

14. The orthopaedic impactor according to claim 1, wherein the first rod diameter is closer to a distal end of the push rod than the second rod diameter and the second rod diameter is closer to a proximal end of the push rod than the first rod diameter.

* * * * *

UNITED STATES PATENT AND TRADEMARK OFFICE
CERTIFICATE OF CORRECTION

PATENT NO. : 10,624,763 B2
APPLICATION NO. : 14/511735
DATED : April 21, 2020
INVENTOR(S) : Conley Page 1 of 1

It is certified that error appears in the above-identified patent and that said Letters Patent is hereby corrected as shown below:

In the Claims

Column 8
At Line 33, in Claim 12, please delete "said interfacing member is split into four wedges", and substitute therefore --each of the at least four sections comprises a wedge--.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*